United States Patent [19]

Mitani et al.

[11] Patent Number: 5,504,010
[45] Date of Patent: Apr. 2, 1996

[54] METHOD FOR TRANSFERRING SAMPLE

[75] Inventors: Toshiharu Mitani; Yasuo Miyoshi, both of Yamaguchi; Yoshiro Hisatomi, Ichihara, all of Japan

[73] Assignee: Mitsui Petrochemical Industries, Ltd., Tokyo, Japan

[21] Appl. No.: 406,788

[22] Filed: Mar. 20, 1995

Related U.S. Application Data

[63] Continuation of Ser. No. 185,160, Jan. 24, 1994, abandoned, which is a continuation of Ser. No. 517,181, May 1, 1990, abandoned.

[30] Foreign Application Priority Data

May 1, 1989  [JP]  Japan .................... 1-112547

[51] Int. Cl.⁶ ............................................ G01N 35/08
[52] U.S. Cl. .................. 436/53; 73/864.33; 73/864.81; 422/81; 422/82; 436/52
[58] Field of Search ................ 422/81, 82; 436/52, 436/53, 180; 73/864.33, 864.81

[56] References Cited

U.S. PATENT DOCUMENTS

| | | | |
|---|---|---|---|
| 2,899,280 | 8/1959 | Whitehead et al. | 422/82 |
| 3,881,872 | 5/1975 | Naono | 422/81 |
| 3,912,452 | 10/1975 | Sodickson et al. | 422/81 |
| 4,148,610 | 4/1979 | Miller et al. | 422/81 |
| 4,398,894 | 8/1983 | Yamamoto | 422/82 |
| 4,526,754 | 7/1985 | Burns et al. | 422/82 |
| 4,853,336 | 8/1989 | Saros et al. | 422/81 |

FOREIGN PATENT DOCUMENTS 8800347  1/1988  WIPO .

OTHER PUBLICATIONS

266B Analytical Chemistry, vol. 57, pp. 2575–2579, Monosegmented System for Continuous Flow Analysis, Spectrophotometric Determination of Chromium(VI), Ammonia, and Phosphorus.

Primary Examiner—James C. Housel
Assistant Examiner—Jan M. Ludlow
Attorney, Agent, or Firm—Sherman and Shalloway

[57] ABSTRACT

A sample to be analyzed is taken from a flow line of a production process and transferred through a slender pipe to an analyzing device. The transfer is accomplished using a pressurized liquid with a segment gas being interposed between the sample and the pressurized liquid. The sample may be fed directly or after mixing with a diluting liquid in a mixing chamber. Samples may be taken at regular and constant time intervals and transferred to the analyzing device stably and over predetermined periods of time.

14 Claims, 2 Drawing Sheets

METHOD FOR TRANSFERRING SAMPLE

This application is a continuation of application Ser. No. 08/185,160, filed Jan. 24, 1994 now abandoned, which is a continuation of Ser. No. 07/517,181, filed May 1, 1990 now abandoned.

BACKGROUND OF THE INVENTION

1. Field of the Invention

This invention relates to a method of transferring a mixture from a reaction process or a production process to an analyzing device to analyze it. More specifically, it relates to a method of transferring a sample of a mixture in the process to an analyzing device remote from the process safely and stably without a substantial change in the composition of the sample within a predetermined period of time.

2. Description Of the Prior Art

It has been the practice to take a small amount of a sample from a process line for producing a chemical compound on an industrial scale in order to control the quality of the compound, and the safety of the process, or to determine the progress of the reaction. Particularly, with the recent automation of the production process, it is necessary to determine the progress of the reaction more accurately, and devices and means for automatically analyzing such a sample periodically have been developed.

Since the analyzing accuracy of an analyzing device for analyzing the sample taken is generally prone to be influenced by exterior factors such as humidity, temperature and vibration, it is rare that the site of taking a sample to be analyzed is near the place at which the analyzing device for analyzing the sample is set up, and they are considerably separated from each other, and at times as remote as more than 100 meters.

Transfer of the sample to such a remote analyzing device is carried out, for example as described in U.S. Pat. No. 4,148,610, by dissolving the sample in a solvent by stirring with a gas, and then sending the solution containing the sample in an analysis line using a pressurized gas and conveying it to the place where the analysis device is set up.

However, because this method sends a sample solution to the place of the analysis device by using a pressurized gas, the time of arrival of the analysis sample will be markedly delayed because of the expansion or shrinkage of the pressurized gas or its leakage, and at times, the movement of the sample might be stopped and an accurate analysis of the sample might fail. The length of the analyzing sample in the analysis line is generally several tens of centimeters. When the same sample is to be analyzed by using a number of analyzing devices, a length of about 1 to 2 meters may be necessary. When a gas is used as a pressurized medium for transfer, the time required for the Sample to arrive at the analyzing device may differ with considerable errors depending upon the expansion or Shrinkage of the pressurized gas caused by temperature changes. Sometimes, the solvent dissolving the sample is evaporated in the pressurized gas to precipitate the sample which may narrow the analysis line. In such a case, there are considerable errors in the time of arrival of the sample. In such a case, the concentration of the sample will vary and the sample may not be able to be analyzed accurately. In the conventional method of transferring the sample with a pressurized gas, it is difficult to maintain the transferring state of the sample constant. Accordingly, it is very difficult to set the timing of analyzing the sample being transferred through the analysis line.

SUMMARY OF THE INVENTION

A first object of this invention is to provide a method of transferring a sample from various production processes to an analyzing device remote from the processes without causing any substantial change which affects the analysis to the sample.

A second object of this invention is to provide a method of taking a simple from the production process in an actual industrial plant regularly and at a constant time interval and transferring it to an analyzing device stably within a certain fixed period of time.

Another object of this invention is to provide a method of transfer in which when a sample from an actual industrial plant is transferred to an analyzing device continuously, the transfer condition, the transfer time and the transfer timing do not vary from sampling to sampling.

Still another object of this invention is to provide means for transferring a sample which is suitable for taking the sample from a process in an industrial plant at a relatively high frequency per unit time.

A further object of this invention is to provide a continuous sample transfer system including taking a sample from an industrial process, treating of the sample for transfer to an analyzing device, and washing and drying the sample in a line.

Other objects of this invention will be apparent from the following description.

The objects of this invention are achieved in accordance with this invention by (1) a method of tranferring a sample taken from a line of a production process through a slender pipe to an analyzing device, which comprises transferring the sample by a pressurized liquid with a segment gas interposed between the sample and the pressurized liquid; and (2) a method of transferring a sample taken from a line of a production process through a slender pipe to an analyzing device, which comprises mixing the sample with a diluting liquid in a mixing chamber provided near the line of the production process, and transferring the mixed liquid with a pressurized liquid with a segment gas interposed between the mixed liquid and the pressurized liquid.

BRIEF DESCRIPTION OF THE ACCOMPANYING DRAWINGS

Figure 1:
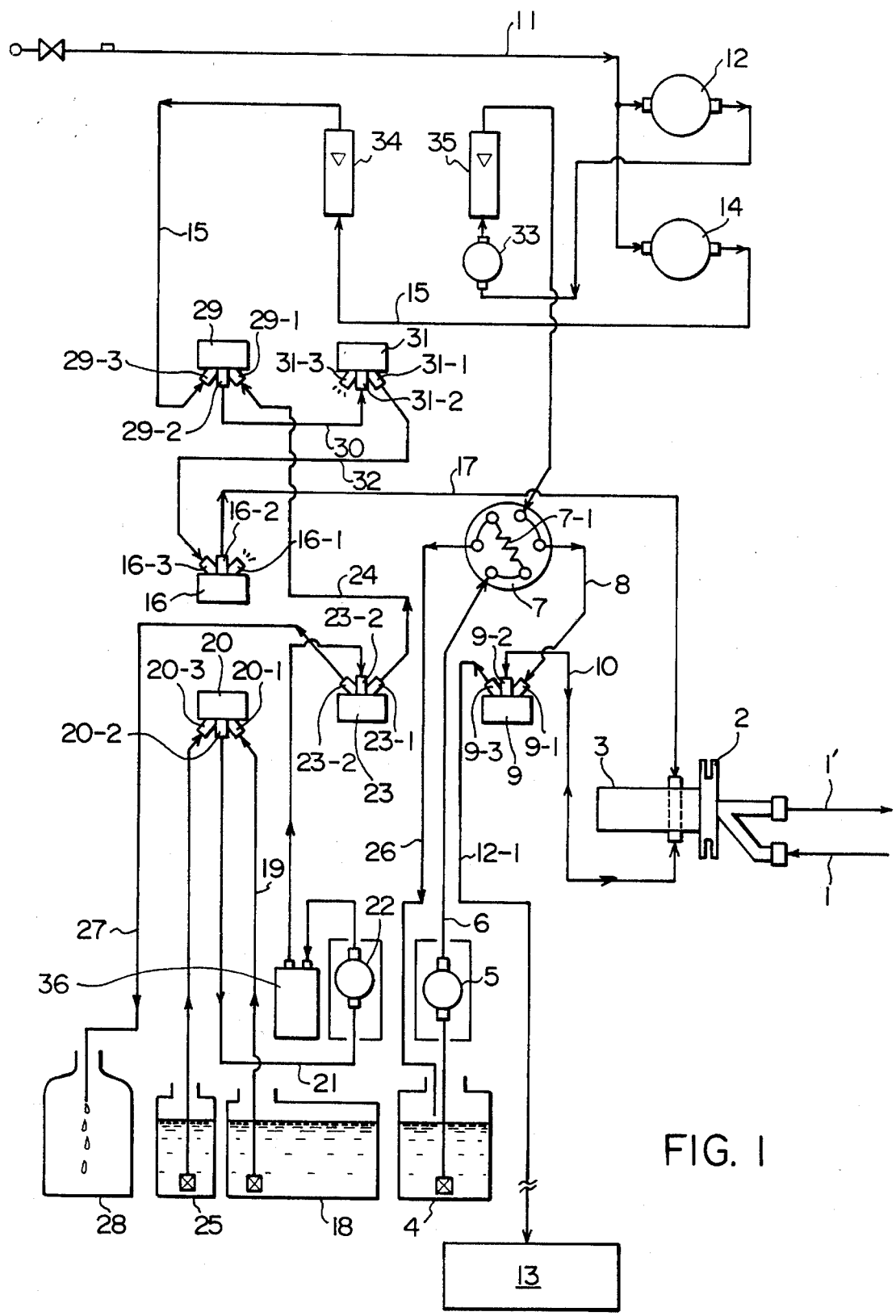
FIG. 1 is an example of flow sheet schematically showing the Steps of the method of this invention.

The reference numerals in FIG. 1 represent the following parts of the apparatus used in the method.

1 ... sampling line,
2 ... sampling device,
3 ... mixing chamber,
4 ... diluting liquid tank,
5 ... motor (or actuator),
7 ... switching valve, 9, 16, 20, 23 . . . three-way slider valves,
12, 14, 33 . . . mass flow valve,
12-1 . . . analyzing line (slender pipe),
13 . . . analyzing device,
18 . . . pressurized liquid tank,
25 . . . washing liquid tank,
28 . . . waste liquor tank,
6, 8, 10, 11, 15, 17, 19, 21, 24, 26, 27 . . . lines
34, 35, 36 . . . flow meters

DESCRIPTION OF THE PREFERRED EMBODIMENTS OF THE INVENTION

The transferring method of this invention will now be described in detail below.

There is no particular limitation on the production processes to which the transferring method of this invention can be applied. Desirably, the method of this invention is advantageously applied to a process in which the state of a line in a production process is analyzed by taking up a sample and the sampling is always necessary, and also if the place of analyzing the sample is remote from the production process.

Specific examples of the production process to which the method of transferring a sample in accordance with this invention include reaction processes such as a synthesis reaction,i a polymerization reaction, a decomposition reaction, an isomerization reaction and a biological reaction, and physical or mechanical processes such as dissolution, mixing, distillation, dispersion, powderization, removing and extraction. Some examples of sampling in the lines of these various production processes are shown below. They are, however, cited for the sake of illustration, and do not limit the present invention.

(i) Sampling of a reaction mixture from a reactor for synthesis reaction of organic compounds as in an oxidation of cumene or oxidation of cymene.

(ii) Sampling of polymer from a polymerization reactor for 4-methylpentene-1.

(iii) Sampling of a cultivation product from a bioreactor.

(iv) Sampling of a mixture from a mixing vessel.

(v) Sampling of a product from a separator such as a distillation column.

The samples taken from the production process line is in a small amount. They may be in the form of a liquid, dispersion, a melt, a gas or a solid, preferably the liquid, dispersion, melt, especially preferably the liquid or dispersion.

The sample taken from the line of the production process is usually sent to an analyzing device through a slender pipe. The slender pipe generally has an inside diameter of about 0.2 mm to about 5 mm, and preferably about 0.5 mm to about 3 mm.

The length of the slender pipe ranging from the line of the production process to which the method of this invention applies to the analyzing device is more effective if it is longer. Generally, the length of the slender pipe is at least 10 m, suitably about 20 to about 500 m, more suitably about 30 m to about 340 m.

The sample or its mixture transferred by the method of this invention is analyzed by various analyzing instruments to be described. Generally, the type and composition of a specific compound, the degree of polymerization, water content, pH, the degree of dispersion, purity and enzyme activity are analyzed.

The transferring methods of this invention are described by using FIG. 1. FIG. 1 shows an embodiment in which the sample taken from the production line is mixed with a diluting liquid in a mixing chamber, and the mixed liquid is transferred through the slender pipe. The method of this invention is of course applicable to an embodiment in which a sample as taken from the production process is directly transferred. The method of this invention of transferring the sample to be analyzed will be described with reference to FIG. 1.

The sample may be taken directly from the process line. As shown in FIG. 1, the sampling line 1 is introduced into the sampling device 2 from the process line, (not shown) and in this sampling device 2, a required amount of the sample may be taken. The sample may be taken quantitatively in the sampling device 2 by utilizing a system (not shown) provided in the device. The amount of the sample taken by the sampling device may be properly determined depending upon the method of analysis and the type of the sample. Usually, it is about 50 to about 1000 mg, or about 0.05 to about 1 ml. The remainder of the sample left after Sampling is returned to the process line from the sample line 1'.

The sample taken may be mixed with a small amount of a solvent (diluting liquid) in the mixing chamber 3 installed adjacent to the sampling device 2.

The diluting solvent introduced into the mixing chamber 3 is sent under pressure to the switching valve 7 in the line 6 by means of a liquid-sending pump 5 from the diluting liquid tank 4. The diluting liquid sent to the switching valve 7 is taken in an amount sufficient to dissolve or disperse the sample taken by the sampling device 2. The diluted liquid is then sent to the three-way slider valve 9. In the three-way slider valve 9, the valve 9-3 to which the line 10 is connected is closed, and the diluting liquid is passed through the line 10 via the valve 9-2 and is introduced into the mixing chamber 3.

The sample and the diluting liquid introduced into the mixing chamber 3 as above are stirred by a stirring means (not shown) provided in the mixing chamber 3 to form a uniform solution or dispersion. There is no particular limitation on the stirring means. For example, the stirring may be mechanically carried out by using stirring blades. Preferably, the stirring may be effected by using a gas. A gas used for stirring comes from the gas introduction line 11, is adjusted in flow rate by a mass flow valve 12, and sent to the switching valve 7. After the diluting liquid is sent from the switching valve 7, the gas is sent to the mixing chamber 3 at the line 10 via the three,way slider valve 9. Alternatively, the gas is introduced together with the diluting liquid into the mixing chamber 3 at the line 10 via the three-way slider valve 9. By bubbling the gas within the mixing chamber 3, the sample and the diluting liquid are mixed, and a uniform solution or dispersion is prepared.

The amount of the diluting liquid to be introduced into the mixing chamber 3 may be determined in conformity to the type and sensitivity of the analyzing device. Preferably, the amount of the diluting liquid is such that the concentration of the sample is 2 to 20% by volume if the analyzing device is a gas-chromatographic analyzing device, and the concentration of the sample is 2 to 20% by volume if the analyzing device is an iodometric device. Furthermore, depending upon the type of the sample or the purpose of analysis, various liquids such as water, alcohols, ketones, esters, ethers, aromatic hydrocarbons and aliphatic hydrocarbons may be used as the diluting liquid. The gas to be used for stirring with may be air. The oxidative decompo sition of the sample at the time of stirring may be effectively prevented by using inert gases such as nitrogen gas and argon gas.

The solution or dispersion of the sample prepared as above in the mixing chamber 3 is transferred to the analyzing device 13 by a transferring liquid with a segment gas interposed between the sample and the transferring liquid.

Specifically, the gas taken from the gas introduction line 11 is introduced into the three-way slider valve 29 through the line 15, and further advances to the three-way slider valve 31 via the line 30. It further passes through the line 32 and then the three-way slider valve 16. The pipe length of the line 17 becomes the length of the segment gas. The volume of the segment gas is desirably 1 ml. After a small amount of the gas (segment gas) is sent in the direction of the mixing chamber 3, the valve 16-3 of the three-way slider valve is immediately closed. As soon as the valve 16-3 is closed, the valve 16-2 is released to introduce the pressurized liquid from the valve 16-2. The transferring pressurized liquid stored in the pressurized liquid tank 18 is sent to the three-way slider valve 20 by operating the liquid transferring pump 22. The valve 20-3 of the three-way slider valve is closed while the valves 20-1 and 20-2 are released. The pressurized liquid introduced into the three-way slider valve 20 via the line 19 is introduced into the three-way slider valve 23 via the line 21 and the liquid transferring pump 22.

By closing the valve 23-3 of the three-way slider valve 23 and releasing the valve 23-1, the transferring liquid is introduced into the three-way slider valve 29 from the valve 23-1 after passing through the line 24.

By closing the valve 29-3 and releasing the valve 29-1, this transferring liquid is sent to the three-way slider valve 31 via the line 30. By closing the valve 31-3 of the three-way valve 31 and releasing its valve 31-1, the transferring liquid passes through the line 32 and the valve 16-1 of the three-way slider valve 16 and sent into the mixing chamber 3 from the line 17.

The transfer ring pressurized liquid is introduced into the mixing chamber 3 as soon as the segment gas is introduced into it. The sample solution within the mixing chamber 3 is sent by the pressure of the pressurized liquid in the direction of the three-way slider valve 9 through the line 10. The pressure of the pressurized liquid may be set properly by the length of the analyzing line, but is usually 0.1 to 2 kg/cm$^2$-G, preferably 0.2 to 1.0 kg/cm$^2$-G. By adjusting the original pressure of the segment gas as above, the flow rate of the segment gas which is, for example, a nitrogen gas, may be adjusted to about 1 to 100 ml/minute, preferably 10 to 60 ml/minute.

When the pressurized gas is sent into the mixing chamber 3, the valve 9-1 in the three-way slider valve 9 is closed and the valve 9-3 is released. As a result, the sample solution or dispersion, the segment gas and the pressurized liquid discharged from the mixing chamber 3 are sent out from the analyzing line 12-1 in this order from the valve 9-3 of the three-way slider valve. By continuing to operate the liquid transferring motor 12, the sample solution or dispersion is transferred to the analyzing device 13 through the analysis line 12-1 with the transferring liquid pressurized by the transferring motor 22.

In the above method, the segment gas may be used in such an amount as can partition between the sample solution and the pressurized liquid. The volume of the segment gas is usually 1/10 to 3 times, preferably 1/2 to 1 time, that of the volume of the sample solution. If the amount of the segment gas is smaller than the above range, the sample solution cannot sufficiently be partitioned from the pressurized liquid. Further, if the amount of the segment gas is large, the volume of the segment gas varies greatly owing to such conditions as temperature, pressure, the concentration of the sample of the analysis solution owing to a change in the gas volume, and the dissipation of the solvent may make it impossible to increase the analyzing accuracy sufficiently. The volume of the segment gas denotes that at the pressure of transferring the sample calculated for the temperature and pressure of the sample solution or dispersion.

Desirably, the amount of the segment gas is such that it becomes about 0.1 to about 3 ml, preferably about 0.5 to about 1 ml, of cross sectional area of the slender pipe for transferring the sample or its mixture and being taken at right angles to the flowing direction. The volume of the gas at this time is that at the temperature and pressure at the time of transferring the sample or the sample mixture. The above-mentioned sectional area taken at right angles to the flowing direction means the substantial area (generally calculated from the inside diameter of the pipe through which the sample or its mixture flows in the slender pipe. There is no particular limitation on the pressure-transferring liquid used in the above described transferring method. Desirably, it should be a liquid which can effect pressure transferring while washing the analysis line. Examples of suck liquid are water, alcohols, ketones, esters, aliphatic hydrocarbons and aromatic hydrocarbons which may be used singly or in combination. The segment gas that may be used in this invention is not particularly limited if it is a gas which has no reactivity with a sample to be analyzed. Usually, the same gases as exemplified above with regard to the stirring with the gases may be cited.

The sample solution or dispersion transferred to the analyzing device is discharged after it is analyzed in the analyzing device 13.

Since in the method of this invention, the sample to be analyzed is tranferred by using the liquid, this liquid has an action of washing the analysis line during transfer of the sample. Preferably, after the analysis is over, a washing solution is allowed to flow through the system to wash the slider valves, the mixing chamber, and pipings.

Specifically, the washing operation is done by operating the liquid transfer pump 22 while the valve 20-1 is closed and the valve 20-3 is opened. As a result, the washing liquid filled in a washing liquid tank 25 is introduced into the three-way slider valves 20, and through the line 21, the washing liquid is introduced into the three-way slider valve 23, and via the line 24, the washing liquid is introduced into the mixing chamber 3 through the three-way slider valve 16 to wash the mixing chamber 3. Furthermore, this washing liquid is introduced into the three-way slider valve 9 via the line 10 from the mixing chamber 3. Then, the washing liquid is passed through the analysis line 12-1 to wash the inside of the analyzing device 13, and finally discharged.

There is no particular limitation on the washing liquid used to wash the system. There may be used various solvents such as water, alcohols, ketones, esters, aliphatic hydrocarbons and aromatic hydrocarbons either singly or in combination.

Usually, after the inside of the system has been washed as above, it is preferable to pass a dry gas through the system to remove the washing liquid.

The drying operation is carried out, for example, in the following manner after the washing is carried out as above. For example, a gas introduced from the gas introducing tube 11 is introduced into the three-way slider valve 16 via the line 15 by utilizing the mass flow valve 14. Then, it is successively allowed to flow through the mixing chamber 3, the line 10 and the three-way slider valve 9. Finally, from the analysis line 12-1, the gas is introduced into the inside of the analyzing device 13 and discharged.

After the end of the drying operation, a sample to be analyzed is taken again by the same operation as above, and the above operation is repreated.

In the above method, the excess of the diluting liquid is returned for reuse to the diluting liquid tank 4 by the line 26 leading from the switching valve 7.

A portion of the pressurized transfer liquid or the washing liquid is discarded into the waste liquor tank 28 by the waste liquor tube 27 from the valve 23-3 provided in the three-way slider valve 23.

The above method of transferring the sample to be analyzed may be applied to those samples which are in the form of a solution, a dispersion, a melt or a gas, but advantageously to a liquid, a dispersion or a melt which has good flowability. When a sample of a low viscosity is to be transferred or the analysis method cannot use a dilute sample, the step of diluting the sample with a diluting liquid may be omitted.

The analyzing method that can be used in this invention is not particularly limited. Various analyzing methods may be used. Examples include gas chromatography, liquid chromatography, ion chromatography, iodometry, ion meter, specrophotometry, atomic absorption spectroscopy and plasma emission spectrometry.

The method of transferring a sample to be analyzed in accordance with this invention differs from conventional methods, and is characterized by transferring the sample with a pressurized gas using a segment gas interposed between the sample and the liquid. By transferring the sample with using a liquid, there is a very little error in the time required for the sample to arrive at an analyzing device set up at a place remote from the sampling place. Accordindgly, the decreasing of the analytical accuracy owing to the improper timing in analyzing the sample can be small.

By interposing the segment gas between the analytical sample and the pressure-transferring liquid, the sample does not mix up with the pressurized liquid, and therefore the decrease of the analytical accuracy that is due to the mixing of the analytical sample with the transferring liquid can be prevented.

The present invention also has the advantage that strict sealing is not required as in the case of using a gas as a pressure-transferring medium.

Since according to the present invention, the sample to be analyzed is transferred by using a pressurized liquid via a segment gas interposed between the pressurized transferring liquid and the sample, it has a much improved analytical accuracy in comparison with transferring it with a pressurized gas. Accordingly, by utilizing the transferring method of this invention, an automatic control of a reaction can be carried out very well. By using the transferring method of this invention in a quality controlling step, the variations in the product grade can be reduced.

The transferring method of this invention can be utilized in an industrial production line as well as in the production of a chemical compound on a laboratory level.

The following example will illustrate the method of this invention more specifically.

EXAMPLE (1) The automatic analyzer system used in this example was comprised of a sampling sequence, an analyzing sequence and a data processing sequence, and these units operated with good timing.

In this example, the sequence was selected so that an analyzing sample (the reaction mixture obtained by oxidizing diisopropylbenzene with molecular oxygen) was taken at a rate of once/an hour and the analysis was carried out continuously.

The sampling device transferred 1 ml of methanol as a diluting solvent to the mixing chamber. Forty seconds later, 50 microliters of a sample was taken from the sampling valve and bubbled with nitrogen as a stirring gas. The sample so diluted was transferred to the analyzing device at a rate of 4 ml/min. with a 1:1 by volume mixture of water+ acetone as a pressurized liquid using nitrogen from line 17 filled with nitrogen as a segment gas. Sixty seconds after the starting of the transfer, the pressurized liquid was switched to a washing liquid (acetone), and the sample was transferred to the analyzing device. The washing liquid was passed at a rate of 4 ml/min. The pressure of the pressurized liquid and the washing liquid was 150 kg/cm$^2$ at the highest. The sample was transferred from the mixing chamber to the analyzing device through a line having an inside diameter of 1 mm and a length of about 30 m. The length of the sample portion dissolved in methanol as the diluting solvent was about 120 cm, and the length of the segment gas portion was about 100 cm. The length of the pressurized liquid was about 50 cm, and the length of the washing liquid portion was about 2730 cm. They moved in this sequence. When the sample in this state arrived at the analyzing device located 30 m away, the sensor detected the arrival of the sample and the sample was injected into four analyzing devices by the sampling means.

(2) In this example, the entirely automated analysis was carried out for 30 days by using the automatic analyzing system. The total number of analyses was 617. By the analyzing operation, the total amount of a peroxide in the sample (the oxidation reaction mixture) was measured by iodometry, and the total amount of the monohydroperoxide in the sample was measured by liquid chromatography. Water concentration was analyzed by measuring the absorbance. In addition to the above automated analysis method, the analysis was carried out by a conventional method in which the sample was not tranferred, but the sample as taken was introduced into the analyzing devices by hand. A known floor injection method was used in this conventional method.

Figure 2:
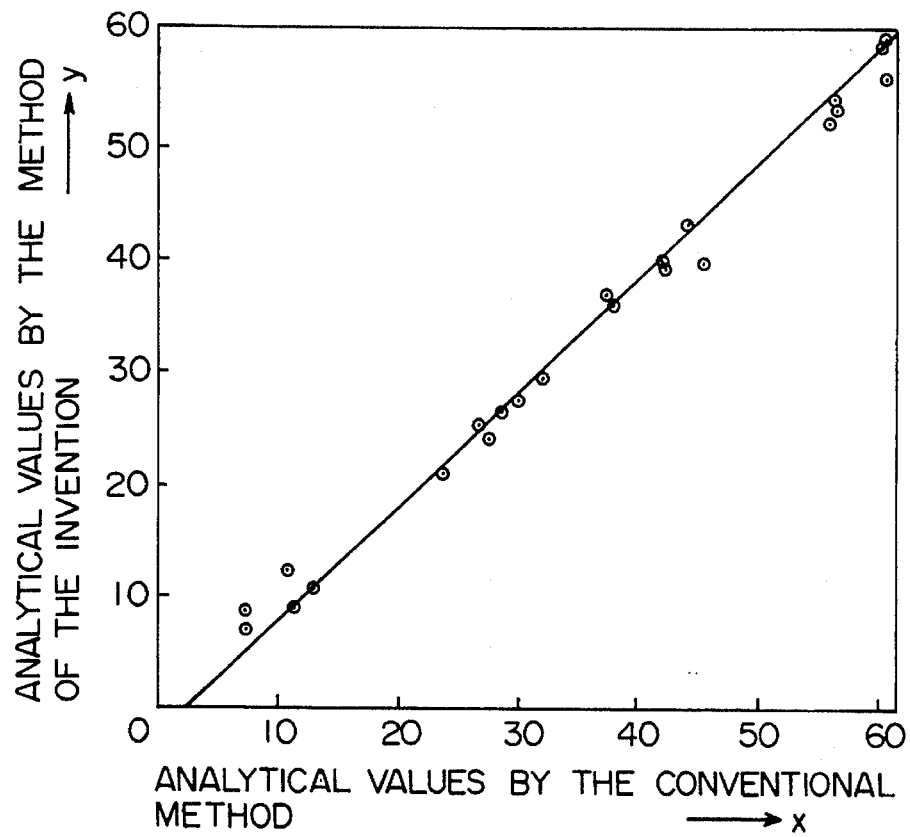
FIG. 2 is a diagram showing the analysis value of the total amount of a peroxide in the Example of this invention in relation to the analysis value obtained by a conventional method.
Figure 3:
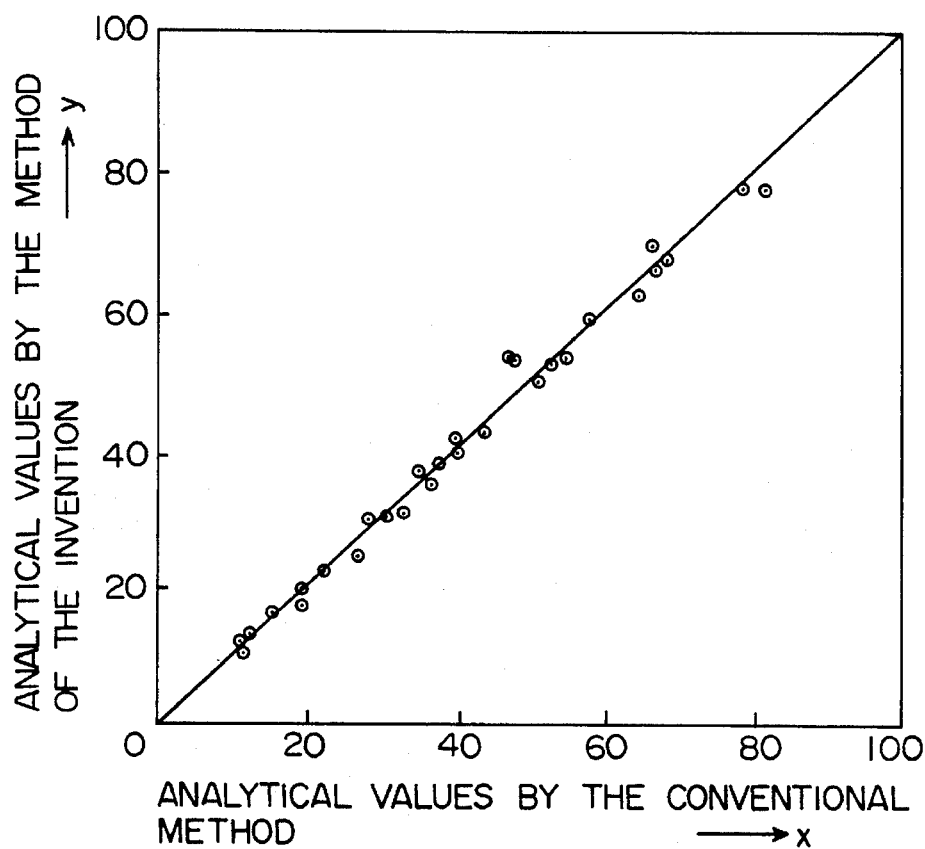
FIG. 3 is a diagram showing the analysis value of the total amount of monohydroperoxide in the Example of this invention in relation to the analysis value obtained by a conventional method.

The total amounts of the peroxide obtained by the two methods are shown in FIG. 2, and the total amounts of the monohydroperoxide obtained by the two methods are shown in FIG. 3.

In FIG. 2, the regression line is y=1.0156x−5.2834 wherein x is the analysis value obtained by the conventional method and y is the analysis value obtained by the method of this invention. r=0.992 (r:coefficient of correlation) and n=54 (n:times of analysis). By the method of this invention, the analysis value was slightly lower, but the correlation was very high.

In FIG. 3, the regression line is y=0.9837x+0.3153 wherein x is the analysis value obtained by the conventional method and y is the analysis value obtained by the method of this invention. r=0.996, and n=34. The correlation was very high, and there was no deviation.

(3) As to the reproducibility of the analyzing method of this invention, the same sample was repeatedly used in the oxidation reaction above, and the measuring accuracy on repetition was determined. In the total hydroperoxide analysis, the relative error was 5.4%, and in the monohydroperoxide analysis, it was 5.1%.

In the water analysis by calorimetry the repeating accuracy was 2.4% in terms of relative error.

(4) The errors in the mixing chamber and in the portion of the line leading from it to the analyzing device were examined by the following procedure.

Water was circulated as a sample through a sample line, and 50 microliters of this water was taken into the mixing chamber. Then, the water was mixed with 1 ml of methanol. This mixture was transferred under pressure to a site 30 m away by using the same pressurized liquid and washing liquid as used in section (1), and then its weight was measured. The measurement was conducted six times, and the relative errors were determined.

| N | Weight (g) |
|---|---|
| 1 | 0.8331 |
| 2 | 0.8529 |
| 3 | 0.8349 |
| 4 | 0.8572 |
| 5 | 0.8530 |
| 6 | 0.8431 |
| $\bar{x}$ | 0.8457 |
| $\delta n - 1$ | 0.01020 |
| relative error(*) | 2.4% |

$$(*)\frac{2\delta_{n-1}}{\bar{x}} \times 100$$

The relative error was as small as 2.4%. That this error is small means that in diluting the taken sample with the solvent in the mixing chamber, the reproducibility of preparing the sample is good, and the proportion of a portion of the sample remaining in the wall of the conduit during movement through the conduit portion from the mixing chamber to the analyzing device is very low. If a portion of the sample remains in the wall during transfer through the conduit, the sample portion in the conduit becomes short, and trouble will occur at the time of injecting the sample into the analyzer, and the analytical accuracy will be lowered.

COMPARATIVE EXAMPLE

In section (1) of Example, the sample was transferred under pressure by using nitrogen gas instead of the pressurized liquid and the washing liquid. Otherwise, in the same way as in Example (1), the amounts of the hydroperoxide (T-HPO) and the monohydroperoxide (MHP) were analyzed 9 times in total using the same sample. The results are shown in the following table.

| | Analysis | | | | | | | | | |
|---|---|---|---|---|---|---|---|---|---|---|
| | 1 | 2 | 3 | 4 | 5 | 6 | 7 | 8 | 9 | |
| T-HPO | 31.9 | 31.8 | 31.1 | 30.8 | 33.9 | 33.4 | 30.0 | 31.5 | 31.5 | *1 |
| MHP | 12.0 | 13.1 | 7.3 | 8.0 | 12.8 | 12.8 | 15.4 | 13.8 | 13.3 | *2 |
| Water | 17.8 | 18.6 | 18.5 | 19.1 | 19.1 | 19.4 | 20.5 | 20.8 | 21.0 | *3 |

*1 $\bar{x} = 32.0, \delta_{n-1} = 1.0934, \frac{2\delta_{n-1}}{\bar{x}} \times 100 = 6.84\%$

*2 $\bar{x} = 12.06, \delta_{n-1} = 2.670, \frac{2\delta_{n-1}}{\bar{x}} \times 100 = 44.3\%$

*3 $\bar{x} = 19.42, \delta_{n-1} = 1.1133, \frac{2\delta_{n-1}}{\bar{x}} \times 100 = 11.5\%?$ As compared with the method of the present invention, the relative errors were considerably high.

We claim:

1. A method of transferring a sample from a production line through a sample transfer pipe to an analyzing device which is remote from the production line, comprising the sequential steps of:

a) removing a sample from the production line;

b) introducing the sample into a cleaned and dry sample transfer pipe;

c) introducing a segment gas into the transfer pipe;

d) passing a pressurized transferring liquid through a liquid transferring pump and introducing the resulting transferring pressurized liquid into the transfer pipe whereby said segment gas is interposed between the sample and the pressurized liquid and wherein the pressurized liquid is in direct contact with the inner surface of the transfer pipe and washes the transfer pipe and propels the sample through the transfer pipe to the analyzing device and e) introducing a dry gas into the transfer pipe to thereby remove liquid and dry the transfer pipe.

2. The transferring method according to claim 1 wherein the volume of segment gas introduced in step (c) is 0.1 to 3 times the volume of the sample.

3. The transferring method according to claim 1 wherein the volume of segment gas introduced in step (c) is in the range of from 0.1 to 3 ml/mm$^2$ of the cross-sectional area of the transfer pipe at a right angle to the direction of flow of the sample in the transfer pipe.

4. The transferring method according to claim 1 wherein the sample is a solution, a dispersion or a melt.

5. The transferring method according to claim 1 wherein the sample from step (a) is mixed with a diluting mixture prior to step (b).

6. The transferring method according to claim 1 wherein the segment gas is air, nitrogen or argon gas.

7. The transferring method according to claim 1 wherein the transferring pressurized liquid is selected from the group consisting of water, alcohol, ketone, ester, aliphatic hydrocarbon, aromatic hydrocarbon, and combinations thereof.

8. The method according to claim 1 wherein steps (a) through (e) are repeated at least once.

9. The method according to claim 5 wherein steps (a) through (e) are repeated at least once.

10. The transferring method of claim 1 wherein the sample transfer pipe is at least 10 meters in length.

11. The transferring method of claim 1 wherein the sample transfer pipe is from about 20 to about 500 meters in length.

12. The transferring method of claim 1 wherein the sample transfer pipe is from about 30 meters to about 340 meters in length.

13. The transferring method of claim 1 wherein the sequential steps (a) through (e) are repeated continuously.

14. The transferring method of claim 1 wherein steps (a) through (e) are repeated at intervals.

* * * * *